United States Patent [19]

Bellos et al.

[11] Patent Number: 5,013,452

[45] Date of Patent: May 7, 1991

[54] RESOLUTION OF EMULSIONS FORMED IN THE PRODUCTION OF PHARMACEUTICALS

[75] Inventors: Thomas J. Bellos, St. Louis; Richard D. Keating, Bridgeton, both of Mo.

[73] Assignee: Petrolite Corporation, St. Louis, Mo.

[21] Appl. No.: 445,578

[22] Filed: Dec. 4, 1989

Related U.S. Application Data

[63] Continuation-in-part of Ser. No. 370,501, Jun. 23, 1989.

[51] Int. Cl.$^5$ ............................................. B01D 17/05
[52] U.S. Cl. .................................... 210/708; 210/734; 210/735; 210/736; 252/344; 252/345; 424/123; 435/43
[58] Field of Search ............... 210/708, 729, 732, 734, 210/735, 736; 435/43; 252/344, 345; 424/123

[56] References Cited

U.S. PATENT DOCUMENTS

| | | | |
|---|---|---|---|
| Re. 22,963 | 1/1948 | Monson et al. | 252/344 |
| 2,407,895 | 9/1946 | Monson et al. | 252/344 |
| 2,562,715 | 7/1951 | Heathcote et al. | 260/239.1 |
| 3,147,218 | 9/1964 | Booth et al. | 210/54 |
| 3,240,721 | 3/1966 | Fordyce | 210/735 |
| 3,299,138 | 1/1967 | Sveum et al. | 210/729 |
| 3,490,938 | 1/1970 | Hoover et al. | 117/100 |
| 3,514,398 | 5/1970 | Shaper | 210/54 |
| 3,539,684 | 11/1970 | Hoover | 424/78 |
| 3,632,559 | 1/1972 | Maffer et al. | 260/78 |
| 3,661,784 | 5/1972 | Bellos | 252/49.3 |
| 3,689,468 | 9/1972 | Cenci et al. | 210/735 |
| 3,725,312 | 4/1973 | Panzer et al. | 210/736 |
| 3,738,945 | 6/1973 | Panzer et al. | 260/2 BP |
| 3,751,364 | 8/1973 | Bellos | 252/49.3 |
| 3,782,546 | 1/1974 | Kirwin et al. | 209/166 |
| 3,793,397 | 2/1974 | Lichtenwalter | 260/288 |
| 3,894,944 | 7/1975 | Panzer et al. | 210/54 |
| 3,894,947 | 7/1975 | Panzer et al. | 210/54 |
| 3,917,529 | 11/1975 | Madole et al. | 210/54 |
| 3,953,374 | 4/1976 | Windhager | 252/518 |
| 3,968,037 | 7/1976 | Morgan et al. | 210/47 |
| 3,975,347 | 8/1976 | Phillips et al. | 260/29.2 |
| 4,001,486 | 1/1977 | Phillips | 528/492 |
| 4,040,984 | 8/1977 | Jackson et al. | 252/500 |
| 4,045,244 | 8/1977 | Lange | 134/22 R |
| 4,102,707 | 7/1978 | Lange | 134/22 R |
| 4,104,161 | 8/1978 | Wein | 210/54 |
| 4,110,521 | 8/1978 | Barnett et al. | 526/64 |
| 4,113,709 | 9/1978 | Quinlan | 424/78 |
| 4,118,316 | 10/1978 | Talley et al. | 210/31 |
| 4,120,815 | 10/1978 | Raman | 210/708 |
| 4,132,674 | 1/1979 | Hwang | 252/500 |
| 4,140,798 | 1/1979 | Merianos et al. | 424/325 |
| 4,141,691 | 2/1979 | Antonetti et al. | 44/1 R |
| 4,158,521 | 6/1979 | Anderson et al. | 405/264 |
| 4,343,730 | 8/1982 | Becker et al. | 524/551 |
| 4,454,047 | 6/1984 | Becker et al. | 210/734 |
| 4,505,839 | 3/1985 | Bellos et al. | 252/344 |
| 4,614,593 | 9/1986 | Roark | 210/708 |

Primary Examiner—Peter Hruskoci
Assistant Examiner—Krisanne Shideler
Attorney, Agent, or Firm—Stanley M. Tarter

[57] ABSTRACT

A method for resolving emulsions produced in preparation of pharmaceuticals by fermentation and in other such bioprocesses is disclosed. The method comprises adding an effective amount of a demulsifier to an emulsion containing fermentation product that includes a pharmaceutical which is desired to be extracted from the emulsion. The demulsifier comprises a nitrogen composition that is selected from among certain quaternized and unquaternized polyoxyalkylated amines, their conjugate acid salts, quaternized and unquaternized condensation product formed by heating an oxyalkylated amine under dehydration condensation conditions to product a polyoxyalkylated amine of molecular weight of at least 400, conjugate acid salts thereof, quaternized and unquaternized copolymers of an epihalohydrin and an amine selected from the group consisting of lower aliphatic primary amines having from two to about eight carbon atoms and lower aliphatic secondary amines having from two to about eight carbon atoms, polydialkyldiallyl ammonium salts, polymers of acrolamido alkylene quaternary ammonium salts, and mixtures thereof.

20 Claims, No Drawings

RESOLUTION OF EMULSIONS FORMED IN THE PRODUCTION OF PHARMACEUTICALS

CROSS-REFERENCE TO RELATED APPLICATION

This is a continuation-in-part of U.S. patent application Ser. No. 07/370,501, filed Jun. 23, 1989.

BACKGROUND OF THE INVENTION

1. Field of the Invention

The present invention relates to demulsification, and more particularly to resolution of emulsions formed during the preparation of pharmaceuticals and other bioprocessing applications.

2. Description of the Prior Art

In a standard method for preparation of pharmaceuticals such as antibiotics, for example, penicillin or substances obtained from microorganisms such as bacteria, algae or fungi (streptomycin, erythromycin, efrotomycin, etc.), a culture of microorganisms or enzymes or both in a nutriment medium, such as vegetable oil in a water base, ferments to produce a desired pharmaceutical. However, the fermented mass has been found to comprise not only the desired pharmaceutical, but also other organic fermentation products such as a biomass of microorganisms or enzymes, uncoverted nutriment medium, water and surfactant. Thus, the desired pharmaceutical must be extracted from the undesirable components of the fermented mass.

The desired pharmaceutical is extracted first by adjusting the pH of the fermented mass, if required. Depending on the particular culture and desired pharmaceutical, the pH is adjusted either up or down, as necessary, by addition of a base or an acid, respectively, to precipitate or partition the desired pharmaceutical. Shortly before or after adjustment of the pH, an extracting solvent, typically an organic phase such as amyl acetate, methyl ethyl ketone, methyl isobutyl ketone, amyl alcohol, butyl alcohol, benzyl alcohol or the like, is added to extract the desired pharmaceutical from the water phase to the organic phase, and the phases are separated.

Often the water and oil phases are commingled in the form of an emulsion, and so good separation can be difficult to achieve. Similar emulsions may also be encountered in other bioprocessing applications. It is believed that the organic phase typically is emulsified or dispersed in the water phase, although it is possible that the water phase is dispersed or emulsified through the organic phase or that actually an emulsion is dispersed or emulsified through another phase such as water.

Nevertheless, depending on the components, some emulsions eventually break by themselves, that is, such emulsions have only "temporary stability" and over time and with the aid of gravity or centrifugation the emulsion separates into distinct layers. However, more commonly, a demulsifier is added to encourage or initiate separation by gravity or centrifugation. Ordinarily, sodium chloride or another inorganic salt or a demulsifier such as DEMULSO I or III (trade designations of Petrolite Corp.) is employed as a demulsifier.

In any event, upon separation, a solvent phase and a water phase are formed. The solvent phase comprises the desired pharmaceutical, solvent and small amounts of water and other impurities, such as organic material, the structure of which may be similar to that of the desired pharmaceutical and other undesirable components dissolved in the solvent. The water phase comprises the remaining components, including the biomass of the microorganisms or enzymes, and there may be a small amount of the desired pharmaceutical dissolved in the water and contained in the biomass.

The solvent phase may be cleaned further after separation from the water phase by adding clean water. By adjusting the pH of the mixture, the desired pharmaceutical sometimes can be shifted to either the water or the organic phase in order to simplify isolation of the pharmaceutical. By a second separation step, the desired phase may be isolated. If the addition of water forms a secondary emulsion, separation may be accomplished as described for the first emulsion.

When the phase containing the desired pharmaceutical has been cleaned to the desired level, excess solvent or water, depending on the phase in which the pharmaceutical is held, can be evaporated off.

Conventional methods for demulsification and separation of phases have several drawbacks. For example, although inorganic salts such as sodium chloride are routinely used as demulsifiers, they do not perform as well as desired. Thus, the phase separation can take place more slowly than desired, and the separation tends to involve a relatively large, indistinct interface, with poor segregation of components into the separate phases. For example, a significant portion of the desired pharmaceutical is often entrapped within cells of the biomass. As a result, recovery of the pharmaceutical typically has been found to be as low as 80%.

Other demulsifiers have been used to resolve such emulsions, but are limited in that they resolve only certain of such emulsions. Moreover, although they resolve the phases more quickly, clearly and thoroughly than do the inorganic salts, even better and faster phase separation is desirable.

On the other hand, a variety of demulsifiers have been used in conjunction with emulsions formed in extraction and production of petroleum-based oils from oil fields. Conventionally, oil field chemistry has not been considered in relation to pharmaceutical processes. In particular, oil field demulsifiers conventionally have not been considered as demulsifiers of emulsions formed during the preparation of pharmaceuticals.

Several factors may contribute to the fact that oil field demulsifiers conventionally have not been considered for resolving emulsions produced in the preparation of pharmaceuticals. Oil field techniques and pharmaceutical processes are extremely disparate arts and one skilled in one of the arts typically would be unknowledgable about the other art. Moreover, even if one were skilled in both arts, oil field emulsions generally are recognized to respond differently to demulsifiers than do emulsions formed in pharmaceutical preparation. Thus, oil field demulsifiers generally have not been employed in resolving pharmaceutical related emulsions.

SUMMARY OF THE INVENTION

Briefly, therefore, the present invention is directed to a novel method for resolving emulsions produced in preparation of pharmaceuticals such as by fermentation or in other such bioprocessing applications. The method comprises adding an effective amount of a demulsifier to an emulsion containing fermentation product that includes a pharmaceutical which is desired to be extracted from the emulsion. The demulsifier comprises a nitrogen composition that is selected from among (a) polyoxyalkylated amines that have been derived from amines having about six to about thirty carbon atoms, (b) polyoxyalkylated amines that have been quaternized to at least some extent and that have been derived from amines having about six to about thirty carbon atoms, (c) conjugate acid salts of polyoxyalkylated amines that have been derived from amines having about six to about thirty carbon atoms, (d) salts of polyoxyalkylated amines that have been quaternized to at least some extent and that have been derived from amines having about six to about thirty carbon atoms, (e) condensation product formed by heating an oxyalkylated amine under dehydration condensation conditions to produce a polyoxyalkylated amine of molecular weight of at least about 400, (f) conjugate acid salts of said condensation product, (g) said condensation product that has been quaternized to at least some extent, (h) conjugate acid salts of said condensation product that have been quaternized to at least some extent, (i) copolymers of an epihalohydrin and an amine selected from the group consisting of lower aliphatic primary amines having from two to about eight carbon atoms and lower aliphatic secondary amines having from two to about eight carbon atoms, (j) such copolymers of an epihalohydrin and a lower aliphatic primary monoamine having from two to about eight carbon atoms, in which at least some of the nitrogen atoms of the copolymers therein have been quaternized, (k) polydialkyldiallyl ammonium salts, (l) polymers of acrylamido alkylene quaternary ammonium salts, and (m) mixtures thereof.

Among the several advantages found to be achieved by the present invention, therefore, may be noted the provision of a method for resolving emulsions produced during the processing of fermentation products which resolves the emulsions more quickly than do the demulsifiers conventionally employed; the provision of such method which resolves the emulsion more thoroughly than do the demulsifiers conventionally employed; the provision of such method which produces a more defined interface than do the demulsifiers conventionally employed; and the provision of such method which demulsifies a variety of such emulsions.

DESCRIPTION OF THE PREFERRED EMBODIMENTS

In accordance with the present invention, it has been discovered that certain demulsifiers found useful in the oil field are surprisingly effective demulsifiers for resolving emulsions produced in preparation of pharmaceuticals or in other such bioprocesses. The effectiveness of such demulsifiers is particularly surprising in view of the fact that other oil field demulsifiers have been shown to be ineffective in resolving pharmaceutical-related emulsions. Although oil field demulsifiers function in many industrial applications, their use in pharmaceutical processes is not generally recognized.

One class of such effective demulsifiers are polyoxyalkylated amines derived from amines having from about six to about thirty carbon atoms. Moreover, the conjugate acid salts of such polyoxyalkylated amines have also been found to be effective demulsifiers for pharmaceutical emulsions, as have quaternaries formed by quaternizing such polyoxyalkylated amines to at least some extent. The salts of such quaternaries also have been found to be effective for such uses.

It is possible, though not known to the inventors herein, that polyoxyalkylated amines might have been used commercially as demulsifiers in the pharmaceutical industry. Regardless, such amines have now been found to be effective demulsifiers for pharmaceutical emulsions. In addition, it now has also been discovered that, surprisingly, not only are such polyoxyalkylated amines effective, but when such polyoxyalkylated amines have been converted to their conjugate acid salts, such as by addition of acid, or have been quaternized to at least some extent, or when such quaternized composition has been converted to its conjugate acid salt, the compositions thus produced in many cases surprisingly are even more effective demulsifiers of pharmaceutical emulsions than are the polyoxyalkylated amines themselves. It is not believed that such salts and quaternaries conventionally have been employed for such purposes.

Another class of such demulsifiers consists of the condensation product formed by oxyalkylating an amine, such as a monoamine, a diamine or a triamine, (the amine having, for example, about six to about thirty carbon atoms) with an epoxide, and then polymerizing the oxyalkylated amine by removal of water so as to join at least two oxyalkylated molecules by the formation of an ether linkage, thereby increasing the molecular weight. The quaternaries of the condensation product are formed by reacting the condensation produce with an alkylating agent to quaternize the condensation product to at least some extent, and have also been found to be superior demulsifiers for resolving such emulsions. Alternatively, the condensation product may be converted to its conjugate acid salts or the residual amines in the quaternaries likewise may be converted to their conjugate acid salts. Such compositions have also been found to be effective demulsifiers.

Such condensed demulsifiers conventionally have been employed variously as oil field demulsifiers where the emulsions typically contain less than about 1% oil-in-water, underwater lubricants, cleansers for removal of solids and oil from dirty water, dewatering agents for high solid concentration sludges or agents for removing particulate matter such as iron or oil or a combination thereof in steel mills.

Other classes of surprisingly effective demulsifiers are copolymers of a lower aliphatic primary or secondary amine and an epihalohydrin, quaternaries of such copolymers, polydialkyldiallyl ammonium salts, and polymers of acrylamido alkylene quaternary ammonium salts. The effectiveness of such demulsifiers is in stark and surprising contrast to the ineffectiveness of certain other oil field demulsifiers, such as dithiocarbamate compounds or copolymers of acrylamide and sodium acrylate, to resolve emulsions produced in preparation of pharmaceuticals.

The polyoxylated amine salts, quaternized polyoxyalkylated amines and related salts of the first class of demulsifiers noted above may be prepared first by polyoxyalkylating an amine by standard techniques. Suitable amines should have from about six to about thirty carbon atoms. Thus, appropriate amines may include monoamines, preferably primary amines of from about six to about thirty carbon atoms such as $C_{18}H_{35}NH_2$ (i.e., octadecenylamine), diamines of from about six to about thirty carbon atoms such as $C_{18}H_{35}(NH)(CH_2)_3NH_2$ or $C_3H_7(NH)(CH_2)_6NH_2$, triamines of from about six to about thirty carbon atoms such as $C_{18}H_{35}(NH)(CH_2)_3(NH)(CH_2)_3NH_2$ or $C_3H_7(NH)(CH_2)_6(NH)(CH_2)_6NH_2$, or other such monoamines or polyamines or mixtures thereof. Mono-, di- and tri-amines of from about six to about thirty carbon atoms are preferred. It is especially desired that the amine have an alkyl group of from about six to about 22 carbon atoms. Most preferably, the alkyl group is derived a natural fat such as cocoa, tallow, soya or their hydrogenated products. A typical monoamine mixture may include, for example, tetradecylamine (3%), pentadecylamine (0.5%), hexadecylamine (29%), heptadecylamine (1%), octadecylamine (20%), tetradecenylamine (0.5%), hexadecenylamine (2%), and octadecenylamine and octadecadienylamine (44% total), based on weight.

The amine is heated in a reactor vessel to a temperature in the range of from about 80° C. to about 150° C., and an alkylene oxide, preferably of from two to about four carbon atoms such as ethylene oxide, propylene oxide or butylene oxide is metered in slowly for incremental addition. The reactor should be a pressure vessel so that upon the addition of the alkylene oxide, the pressure is about 5 to about 100 p.s.i., depending on the desired relative proportion of alkylene oxide. From about 1 to about 50, preferably from about 1 to about 30, moles of the alkylene oxide may be added per mole of amino groups in the heated amine.

The endpoint may be set at the point of desired degree of polyoxyalkylation and will be apparent to those skilled in the art. The endpoint may be determined by the loss of pressure in the pressure reactor.

The use of a catalyst is optional. If a catalyst is employed, about 0.25% by weight to about 10% by weight of a catalyst (e.g., a catalyst of sodium hydroxide or potassium hydroxide or a $BF_3$ catalyst) may be included in the reaction mixture.

Thus, for example, with respect to $C_{18}H_{35}NH_2$ and ethylene oxide, the reaction may yield a polyoxyalkylated amine of the formula

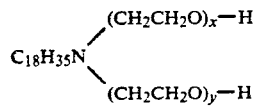

wherein x and y are determined by a statistical distribution such as a Poisson distribution, and the sum of x and y is determined by the molar ratio of reacted ethylene oxide to amino groups.

Likewise, where the amine is $C_{18}H_{35}(NH)(CH_2)_3NH_2$, the reaction may yield a polyoxyakylated amine of the formula

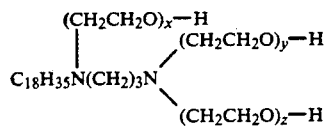

wherein x, y and z are similarly determined by a statistical distribution such as a Poisson distribution, and the sum of x, y and z is determined by the molar ratio of reacted ethylene oxide to amino groups. Triamines and higher polyamines would follow a similar reaction process. With respect to any of the polyoxyalkylated amines, it is noted that some, all or none of the amino groups in an particular molecule may be oxyalkylated.

The polyoxyalkylation reaction product may then be used directly as a demulsifier or, alternatively, either at least partially neutralized to form its conjugate acid salt, which may be used as a demulsifier, or quaternized to at least some extent by reaction with an alkylating agent such as dimethyl sulfate, an alkyl halide (e.g., methyl chloride or methyl iodide), an aralkyl halide (e.g., benzyl chloride) or a bifunctional alkylating agent such as 1,2 dichloroethane or $\beta$, $\beta'$-dichloroethyl ether or a homolog thereof. Combinations of alkylating agents are also suitable. A bifunctional alkylating agent also encourages polymerization of the polyoxyalkylated amine, thereby increasing the molecular weight.

Generally, the alkylating agent is an alkyl halide of from one to about thirty carbon atoms, an alkenyl halide of from one to about thirty carbon atoms, a cycloalkenyl halide of from one to about thirty carbon atoms, an aralkyl halide of from one to about thirty carbon atoms, dimethylsulfate, 1,2 dichloroethane, dichloroethyl ether or a combination thereof. Preferably, the alkylating agent is an alkyl halide of from about one to about six carbon atoms, especially methyl chloride or ethyl chloride, or is an aralkyl halide such as benzyl chloride. Most preferably methyl chloride is used as the alkylating agent.

The alkylating agent to be added to the polyoxyalkylated amine may be undiluted or it may be part of an aqueous solution in which its concentration is at least about 10% by weight. However, if the agent is highly concentrated, i.e., about 50% by weight to about 100%, then it may be desirable to include a base, for example, calcium carbonate, sodium carbonate, potassium carbonate, sodium hydroxide or ammonium hydroxide, to neutralize to at least some degree, acid that may be formed during the reaction. The use of these latter agents can be added incrementally during the alkylating process as needed for pH control.

Preferably the degree of quaternization is from about 25% to about 100%, more preferably about 70% to about 90%, especially about 75%, based on number of nitrogen atoms quaternized. Thus, none, some or all of the nitrogen atoms of any particular molecule may be quaternized. The quaternization product may be used directly as a demulsifier for resolving emulsions produced in preparation of pharmaceuticals by fermentation or in diluted form, such as an aqueous solution, for demulsification. Alternatively, the conjugate acid salts thereof may be used directly or in similar diluted form. Such salts may be formed by addition of an acid, such as hydrochloric acid, to the quaternized oxyalkylated amine.

The condensed polyoxyalkylated amine demulsifiers found to achieve extraordinary results in resolution of emulsions formed during the preparation of pharmaceuticals include the lubricants described in U.S. Pat. Nos. 3,661,784 and 3,751,364, both to Bellos, a co-inventor of the instant application.

Generally, such compositions are prepared by carrying out the polyoxyalkylation process described above followed by dehydration. In more detail, an amine is polyoxyalkylated with an alkylene oxide, preferably of from two to about four carbon atoms (such as ethylene oxide, propylene oxide or butylene oxide) to form an oxyalkylated amine. Although certain diamines are suitable, preferably the amine is a primary or secondary monoamine of the formula:

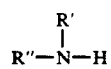

wherein R' and R" are independently selected from among hydrogen and organic radicals of from about six to about 22 carbon atoms, especially alkyl groups of from about six to about 22 carbon atoms, alkenyl groups of from about six to about 22 carbon atoms, alkynyl groups of from about six to about 22 carbon atoms, aryl groups of from about six to about 22 carbon atoms or alkylaryl groups of from about six to about 22 carbon atoms. Some examples of potentially useful groups include phenyl, polyalkylphenyl, alkyl phenyl, chlorophenyl, alkoxyphenyl, naphthyl, alkyl naphthyl, benzyl, furyl, pyranyl, hydrogenated furyl and hydrogented pyranyl. However, at most only one of R' and R" is hydrogen. Monoalkenyl monoamines of from about twelve to about 22 carbon atoms, such as $C_{18}H_{35}NH_2$, are particularly suitable, but any amine having from about six to about thirty carbon atoms is desirable, especially those amines having at least one organic branch of from about six to about 22 carbon atoms.

Suitable diamines may be represented by the formula

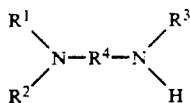

wherein $R^1$, $R^2$ and $R^3$ are independently selected from among hydrogen and organic radicals of from one to about 22 carbon atoms, especially alkyl groups of up to about six carbon atoms, alkenyl groups of up to about six carbon atoms, alkynyl groups of up to about six carbon atoms, aryl groups of up to about six carbon atoms or alkylaryl groups of up to about eight carbon atoms and $R^4$ is selected from among alkylenes of from two to about 22 carbon atoms and arylenes of from three to about 22 carbon atoms, preferably propylene. The alkylene groups may be branched or straight chains, and may be saturated or unsaturated. Thus, an example of $R^4$ is $-CH_2CH_2CH(CH_3)CH_2CH_2-$.

From about 1 to about 50 moles alkylene oxide per mole amine are metered in slowly to a quantity of the amine such that the alkylene oxide is introduced incrementally during the reaction. The reaction is conducted in a pressure reactor at a temperature of from about 80° C. to about 150° C. Generally, the reaction mixture is maintained as water-free as practical. A water content analysis of the amine may be conducted prior to the addition of the alkylene oxide. If the water content is greater than about 0.5% by weight, the amine should be heated in a vacuum (e.g., about 135° C. at 12 to 25 mm Hg) for about one-half to about one hour to reduce the water content to about 0.5% or less by weight.

The polyoxyalkylated amine then is polymerized by dehydration condensation, thereby causing polyoxyalkylated amines to form poly-ethers. That is, the oxalkylated amine is heated to a temperature of from about 100° C. to about 300° C. in the presence of a catalyst, and water and thermal decomposition products (such as glycols and aldehydes) are removed from the reaction mixture throughout the reaction with a condensor and Dean-Stark trap. Preferred catalysts include zinc halides such as zinc chloride, aluminum sulfate, iron halides such as ferrous or ferric chloride, or any of such catalysts in combination with a carboxylic acid such as acetic acid. Dehydration may take place between an unreacted R—NH₂ group or an oxyalkylated R—NH₂ group of one molecule and a hydroxyalkyl group of another molecule to form condensation products and water. However, by this reaction, at least two oxyalkylated molecules also are joined together with the formation of an ether linkage, thereby producing a polyoxyalkylated amine of average molecular weight of at least about 400 and as high as 6,000 to 10,000 or more. In some instances the condensation may yield a product of a relatively low molecular weight of, e.g., 400–4000, while in other instances, the product may have a higher average molecular weight, even in excess of 10,000. These are also useful. It should be further understood that some thermal decomposition takes place to form, inter alia, acetaldehyde and glycols, which condense from the product during reaction.

The reaction may be allowed to run until completion or, if desired, the reaction may be halted when a desired viscosity or molecular weight is attained. Accordingly, polyethers are produced of the form, for example,

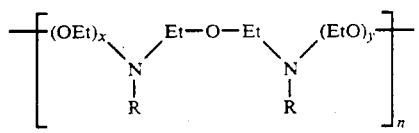

or

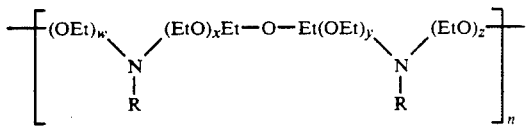

where x and y and w, x, y and z are determined by a statistical distribution such as a Poisson distribution, and the sum of x and y and the sum of w, x, y and z are determined by the relative amount of alkylene oxide added per nitrogen.

Generally, ether formation is limited to a degree by the formation of esters via side reactions (where, for example, acetic acid is used as a cocatalyst); or more precisely, when two hydroxyl terminated molecules condense.

The condensation product may be used directly as a demulsifier for resolving emulsions produced in preparation of pharmaceuticals by fermentation or in diluted form, such as an aqueous solution for demulsification or the acid salts thereof formed by addition of an acid, such as hydrochloric acid, may be used directly or in dilute form.

Alternatively, the quaternaries of the condensed polyoxyalkylated amine may be so used. The quaternaries are formed by quaternizing the condensation product to at least some extent according to the same techniques as discussed for quaternizing the uncondensed polyoxyalkylated amines. That is, by reacting the polymerized oxyalkylated amine with an alkylating agent such as dimethyl sulfate, an alkyl halide (e.g., methyl chloride), an aralkyl halide (e.g. benzyl chloride) or a bifunctional alkylating agent such as 1,2 dichloroethane or β, β'-dichloroethyl ether. A bifunctional alkylating agent also causes further polymerization of the oxyalkylated amine, thereby increasing the molecular weight. Preferred alkylating agents are discussed above with respect to quaternizing the uncondensed polyoxyalkylated amines.

Thus, the alkylating agent to be added to the polymerized oxyalkylated amine may be undiluted or it may be part of an aqueous or a nonaqueous solution (as where an alcohol such as methanol or 2-propanol or a water-alcohol mixture is employed as a diluent) in which its concentration is at least about 10% by weight. However, if the agent is highly concentrated, i.e., about 50% by weight to about 100%, then it may be desirable to include a base, for example, calcium carbonate, sodium carbonate, potassium carbonate, sodium hydroxide or ammonium hydroxide, to neutralize to at least some degree any acid formed during the reaction. The use of these latter agents are usually employed incrementally as needed for pH control during the alkylating process.

Preferably the degree of quaternization is from about 25% to about 100%, more preferably about 70% to about 90%, especially about 75%, based on number of nitrogen atoms quaternized. All, some or none of the nitrogen atoms of any particular molecule may be quaternized. As with the unquaternized condensation products and the acid salt thereof, the quaternary ammonium salt may be used directly as a demulsifier, or it may be diluted first such as by addition of water or other solvent and then applied. Alternatively, residual amines in the quaternaries may be converted to their conjugate acid salts. If desired, the pH of any of the products may be altered to a selected degree by addition of an acid or base so that its addition to the emulsion being treated will not change the pH of the emulsion.

Examples of the copolymers of a lower aliphatic primary or secondary amine and an epihalohydrin that have been found to be effective for resolving pharmaceutical emulsions are in common use in the oil field industry as well as in industrial applications. Especially suitable copolymers include copolymers of dimethylamine and epichlorohydrin as discussed in U.S. Pat. No. 4,001,486 and in U.S. Pat. No. 4,158,521.

Preferably, the mole ratio of the epihalohydrin such as epichlorohydrin to amine such as dimethylamine in the copolymer is in the range of from about 0.25 to about 1, more preferably about 0.75 to about 1.0 (but not limited by this range), and further, the addition of a small amount of a diamine, e.g., ethylene diamine, may be introduced to induce crosslinking between molecules and is sometimes beneficial to the effectiveness of the product. The molecular weight of the copolymer is generally from about 200 to about 50,000 or more. Molecular weights in the range of from about 4,000 to about 50,000 or higher are highly preferred.

It should be recognized that although dimethylamine is particularly desirable because it is readily available, other lower dialkylamines, including diethylamine and dipropylamine, also produce superior results. More generally, the lower aliphatic primary or secondary amine is a monoamine of from two to about eight carbon atoms. The preferred epihalohydrin is epichlorohydrin.

U.S. Pat. No. 3,975,347 describes techniques for preparation of copolymers of lower aliphatic secondary amines and epihalohydrins. The same techniques may be employed with primary amines in place of the secondary amines. Typically, an aqueous solution of from about 50% to about 90% of a lower aliphatic primary or secondary amine such as dimethylamine is heated with agitation to a temperature of about 75° C. to about 95° C. Next, an epihalohydrin such as epichlorohydrin is added with agitation to the heated aqueous solution, preferably in an epihalohydrin to secondary amine molar ratio of from about 0.25:1 to about 1:1, more preferably about 0.75:1 to about 1:1, at a rate sufficient to maintain the reaction temperature between about 75° C. and about 95° C., and such that the concentration of the amine and the epihalohydrin is in the range of from about 60% to about 80% by weight in the aqueous solution.

Although these proportions are preferred, other proportions may be employed and, in particular, it is noted that under some circumstances the amine and epichlorohydrin concentration may be greater than 80% by weight. The reaction product thereby comprises from about 60% to about 85% by weight of a substantially linear polymer of the amine and the epihalohydrin. A small amount (e.g., 2-5%) of a diamine such as ethylene diamine may also be added to the reaction mixture to encourage crosslinking.

When the amine is a secondary amine, the reaction product is a quaternary compound. If the amine is a primary amine, the product is not a quaternary compound, but still may be employed as a demulsifier in this invention. However, if desired, at least some of the nitrogen atoms in the primary amine/epihalohydrin copolymer may be quaternized, and the quaternary composition may be employed as an effective demulsifier for resolving pharmaceutical emulsions. The copolymer may be quaternized by the same techniques as discussed above with respect to the oxyalkylated condensation product. Thus, the copolymer may be quaternized by reaction of the copolymer with an alkylating agent or converted to their conjugate acid salts. The primary or secondary amine-based copolymer or the quaternized primary amine-based copolymer may be used directly or in a diluted form as a demulsifier for resolving emulsions produced in preparation of pharmaceuticals by fermentation.

As with the amine/epihalohydrin copolymers, polydialkyldiallyl ammonium salts found to be effective in resolving the pharmaceutical emulsions likewise are typically employed in the oil field market. The alkyl groups of the generally preferred poly-dialkyldiallyl ammonium salts have from one to about 18 carbon atoms, more preferably from one to about four carbon atoms. Most preferably the alkyl groups are methyls. With respect to the anion of the salts, preferred salts are poly-dialkyldiallyl ammonium halides, especially poly-dialkyldiallyl ammonium chloride.

Poly-dialkyldiallyl ammonium chloride, which is a polymer of dialkyldiallyl ammonium chloride and may be written poly-(dialkyldiallyl ammonium chloride), ordinarily has a molecular weight of from about 10,000 to about 250,000 or more, such as 10,000,000 or more, and is discussed in U.S. Pat. No. 3,782,546, wherein its use as a cationic conditioning agent for potash flotation is disclosed. Molecular weights of about 10,000,000 or more relate to inverse emulsion polymers and/or the dried products produced using the technology of the noted patent. Preferably, however, the molecular weight is from about 10,000 to about 100,000. Commercially available dimethyldiallyl ammonium chloride and polydimethyldiallyl ammonium chloride generally contain a mixture of mono and diallyl forms.

The exact structure of the poly-dialkyldiallyl ammonium salt has been the subject of some uncertainty in the past, and while the noted '546 patent shows a six membered ring, it is now understood that the quaternary may be represented by the formula:

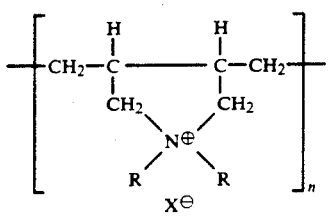

wherein R is an alkyl group of from 1 to about 18 carbon atoms and X is an anion such as a halide (e.g., Cl⁻ or I⁻) or methyl sulfate. Preferably R is a lower alkyl group of 1 to about 4 carbon atoms, most preferably methyl. The preferred anion is chloride. Thus, polydimethyldiallyl ammonium chloride is the most preferred of this class of demulsifiers.

Poly-dialkyldiallyl ammonium salts may be prepared by any of a number of known techniques for polymerizing the cationic monomer. Accordingly, any of the well-known solution, emulsion or suspension techniques are available. U.S. Pat. No. 3,782,546 identifies several U.S. patents which discuss the preparation and use of poly-dialkyldiallyl ammonium chlorides.

As with the other classes of demulsifiers discussed above, poly-dialkyldiallyl ammonium salts may be used directly or in a diluted form as a demulsifier for resolving emulsions produced in preparation of pharmaceuticals by fermentation.

Polymers, i.e., either homopolymers or copolymers, of acrylamido alkylene quaternary ammonium salts found to be useful in this invention include those discussed in U.S. Pat. No. 4,343,730, and generally have a molecular weight of from about 100,000 to more than 2,000,000, preferably about 100,000 to about 2,000,000, most preferably about 1,000,000 to about 2,000,000. It should be noted that as used herein, the term acrylamido alkylene quaternary ammonium salt includes methacrylamido alkylene quaternary ammonium salt.

Thus, the polyquaternary ammonium compounds of the present invention are the linear polymers derived from monoethylenically unsaturated monomeric units comprising from 1 to 100 mole percent, preferably at least 20 mole percent, of amide units of the polymeric formula:

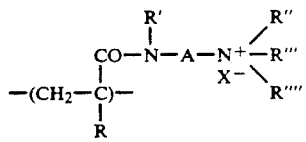

wherein R is hydrogen or methyl, R' is hydrogen or a lower alkyl group having 1 to 4 carbon atoms, A is a straight or branched chain alkylene group having 2 to 10 carbon atoms or a divalent saturated aliphatic group consisting of a plurality of alkylene groups of 2 to 10 carbon atoms each pair of which is connected by an ether oxygen atom, R" and R'" may be (1) separate groups selected individually from the group consisting of alkyl groups having 1 to 12 carbon atoms, hydroxyalkyl groups having 2 to 12 carbon atoms, alkoxyalkyl groups having 2 to 12 carbon atoms, (polyalkoxy)alkyl groups having 2 to 12 carbon atoms, and (2) a single saturated aliphatic group which together with the N atom forms a heterocyclic group containing 5 to 6 atoms in the ring of which 4 to 5 atoms are carbon and which may contain a second atom of the group consisting of O, N, and S, the second atom, if nitrogen, being substituted by hydrogen or an alkyl group having 1 to 18 carbon atoms, R"" is selected from saturated and unsaturated aliphatic hydrocarbon groups having 1 to 18 carbon atoms, (polyalkoxy)alkyl groups having 2 to 18 carbon atoms, alkoxyalkyl groups having 2 to 18 carbon atoms, alkoxyalkyl groups having 2 to 18 carbon atoms, an aralkyl or substituted aralkyl group having 7 to 24 carbon atoms, or a phenoxyalkyl group having 7 to 24 carbon atoms, and X is a negative, salt-forming atom or radical.

The preferred homopolymers and copolymers of U.S. Pat. No. 4,343,730 are believed to be the preferred polymers in the instant invention. Thus, the polymers may be prepared by emulsion polymerization, and a preferred polymer would be a copolymer of a quaternary of dialkylamino alkylacrylamide and acrylamide. Such quaternaries typically have been quaternized to at least some extent with a lower alkyl halide or methyl sulfate.

In the emulsion polymerizationa, a wide variety of aqueous solutions of the monomers can be employed. For example, the monomer content of the solution can be anywhere from about 5 to about 75 weight percent. The particular concentration of monomer, of course, will depend upon the particular monomer and the polymerization temperature. A wide variety of aqueous monomer phase to oil phase ratios, preferably from about 5 to about 95 weight parts of aqueous phase to 95 to 5 parts of oil phase, can also be used during the emulsion polymerization process. A particularly suitable monomer is N,N-dimethylamino-N-propyl-methacrylamide (such as that sold by Jefferson Chemical Company under the trade designation DMAPMA). The cationic material may be N,N-dimethylamino-N-propyl-methacrylamide-N-benzyl ammonium chloride. Alternatively, one can form the polymer derived from the base and the quaternary, and if desired, the residual free amine can be converted to its conjugate acid salt. Similar acrylamides are also suitable.

All such classes of demulsifiers are surprisingly effective in resolving emulsions produced in preparation of certain pharmaceuticals such an antibiotics, for example, penicillin or substances obtained from fungus (streptomycin, erythromycin, efrotomycin, etc.), by fermentation. Such demulsifiers have been found to be remarkably fast acting, with application of a very small amount of the demulsifier (generally about 200 to about 1,000 parts per million by weight of the emulsion) producing a nearly immediate phase separation with an exceptionally clear, well defined interface, and almost all of the desired pharmaceutical segregated into one of the phases. Not only that, the demulsifiers of this invention have been found to be effective for a wide variety of emulsions produced in preparation of various pharmaceuticals by fermentation.

More specifically, upon application of a demulsifier of this invention to such emulsions, the emulsion usually separates immediately into distinct phases with a sharp, well defined interface, and particulate matter in the emulsion being treated is sequestered into a tacky agglomeration in the form of a ball or layer that resides either at the interface or in the aqueous phase. The phase separation is essentially complete, with little or no residual emulsion remaining. Where the desire pharmaceutical resides is dependent or where and how the pharmaceutical manufacturer manipulates the pH. For example, pH adjustment may cause the desired pharmaceutical to collect in the water phase, while a different pH adjustment may cause the desired pharmaceutical to collect in the organic phase.

The emulsions to which the demulsifiers of this invention are applicable are those formed during preparation of pharmaceuticals such an antibiotics, for example, penicillin or substances obtained from microorganisms such as bacteria, algae or fungi (streptomycin, erythromycin, efrotomycin, etc.), in which a culture of microorganisms or enzymes in a nutriment medium, such as vegetable oil in a water base, ferments to produce a desired pharmaceutical. The emulsion comprises an organic solvent, typically amyl acetate or butyl acetate or possibly methyl isobutyl ketone, emulsifiers, nutrient from the nutriment medium, particulate matter including enzymes or microorganisms, and various electrolytes. Such emulsions are produced in a broad range of pH's and the components are present in a variety of relative proportions. Similar emulsions, which also might be treated with the demulsifiers of this invention, may be the result of other bioprocessing applications.

To resolve such emulsions, the demulsifier is applied to the emulsion by addition of an amount corresponding to from about 100 parts by weight to about 10,000 parts by weight of the demulsifier composition of this invention to one million parts by weight of the emulsion. If desired, the demulsifier may be mixed into the emulsion by shaking or stirring. Preferably from about 200 parts by weight to about 1,000 parts by weight of the demulsifier composition to one million parts by weight of the emulsion is added, but about 1,000 parts by weight to about 10,000 parts by weight are also acceptable. The optimal proportion depends on the particular emulsion being treated. Such emulsions typically comprise about 25% by weight to about 75% by weight, often about 50% by weight water. Typically, some such emulsions have first been neutralized to a pH of from about 7 to about 7.4. However, other emulsions have other pH's, and it has been found that the demulsifiers of this invention are applicable over a wide pH range—at least from about 4 to about 9.

It has been found that upon addition of the demulsifier, the emulsion separates almost immediately into two phases with a sharp, well-defined interface, with an agglomeration of the solids in the mixture either at the interface or at the bottom of the mixture.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE 1

Rich extract was obtained from the production of an antibiotic derived from a fungus. The unfiltered fermentation broth was acidified and contacted with methyl isobutyl ketone as an extracting solvent to produce the rich extract. The rich extract was diluted with deionized water and neutralized with sodium hydroxide to a pH of about 7 to about 7.4, and separated into several emulsion test samples of 40 to 50 ml each.

All tests were carried out in centrifuge tubes. For each test, demulsifier was added as a 1% agueous solution and mixed into the emulsions with hand shaking or with the aid to a tube mixer. Some samples were sheared with a homogenizer to simulate the high shear the emulsion will encounter as it enters the full-scale disk centrifuge used in actual processing. All samples were centrifuged in a laboratory model centrifuge for five minutes at 3200 rpm. The tubes were then judged on the amount (percent) of solvent and water recovered, the clarity of the two phases and the amount and relative location of solids in the tubes.

Test samples 1–18 were run with a selection of compounds chosen to represent a wide range of chemistries available within the industrial and oilfield reverse demulsified lines. The demulsifiers tested are designated as follows to correspond to samples of the mixtures which have been found to fall within the indicated viscosity and molecular weight ranges:

| Demulsifier | Active Ingredient |
| --- | --- |
| A | poly (dimethyldiallyl ammonium cnloride); m.w. from 10,000 to 100,000; visc. of about 600–900 cps at 25° C. for 20% active aq. soln. |
| B | poly (diethylamine/epichlorohydrin copolymer); m.w. from 4,000 to 50,000; visc. of about 600–900 cps at 25° C. for 50% active aq. soln. |
| C | copolymer of a mixture of butane diamine, hexane diamine, and 1.2 cyclohexyl diamine and epichlorohydrin; epi/amine ratio of from 0.25 to 1; m.w. from 50,000 to 500,000; visc. of about 450–1400 cps (typically about 650 cps) at 25° C. for 50% aq. soln. |
| D* | low m.w. cationic acrylate dimethyl amino ethyl methacrylate (DMA-EMA); visc. of about 160 cps at 25° C. for 12.5% aq. soln. |
| E* | polyamine ureylene (urea & bis-hexamethylene triamine polymerization reaction product) |
| F* | dithiocarbamate |

*Demulsifier not within the scope of the invention

The compounds were tested and ranked at doses of 250 and 500 ppm, based on the total emulsion volume. The results were as follows with the ranking of the phase clarity from clearest to cloudiest indicated as 1 through 6, respectively:

250 ppm dose of demulsifier:

| Sample | Demulsifier | Emulsion pH | Aqueous Phase Clarity (Rank) | Solvent Phase Clarity (Rank) | Comments |
| --- | --- | --- | --- | --- | --- |
| 3 | A | 7.1 | 3 | 4 | thin interface |
| 5 | B | 7.1 | 1 | 1 | dark interface |
| 7 | C | 7.1 | 5 | 3 | thin interface |
| 13 | D | 7.1 | 6 | 5 | very broad interface |
| 15 | E | 7.1 | 2 | 2 | broad cloudy interface |
| 17 | F | 7.1 | 4 | 6 | bad break; cloudy interface |

500 ppm dose of demulsifiers:

| Sample | Demul-sifier | Emulsion pH | Aqueous Phase Clarity | Solvent Phase Clarity (Rank*) | Comments |
|---|---|---|---|---|---|
| 4 | A | 7.1 | 3 | 5 | slightly cloudy interface |
| 6 | B | 7.1 | 2 | 1 | dark interface |
| 8 | C | 7.1 | 1 | 2 | thin interface |
| 14 | D | 7.1 | 5 | 4 | bad interface |
| 16 | E | 7.1 | 4 | 3 | thin interface |
| 18 | F | 7.1 | 6 | 6 | bad break; cloudy interface |

Of particular importance is the quality of the interface, the aggregate of solids and the quality of the solvent phase where the desired pharmaceutical resides.

EXAMPLE 2

Demulsifiers B and C were selected for additional tests at other doses. These were compared with a blank and samples dosed with NaCl and Akzo D5430, a quaternary fatty acid amine salt from Akzo Chemicals, Inc. The emulsion pH of the samples was 7.1. The results of these tests, samples 19–33, were as follows:

| Sample | Demul-sifier | Dose (ppm) | Solvent Phase Clarity | Aqueous Phase Clarity (Rank*) | Comments |
|---|---|---|---|---|---|
| 25 | B | 300 | excellent | X | good interface; solids dropped |
| 26 | B | 500 | excellent | X | solids dropped |
| 27 | B | 700 | excellent | 3 | solids dropped |
| 28 | C | 300 | excellent | 1 | solids at interface |
| 29 | C | 500 | excellent | X** | solids at interface |
| 30 | C | 700 | excellent | X** | solids at interface |
| 31 | D5430 | 500 | sl. cloudy/dark | 2 | good aggregate, but significant amount of solids in solvent |
| 32 | nothing | | | good | bad interface into solvent; fair aggregate phase |
| 33 | 1% NaCl | | cloudy | good | large interface |

*Rank 1 corresponds to clearest phase.
**Apparent overtreatment

The D5430 produced relatively clear water but appeared to leave traces of solids or water in the solvent layer. The sample treated with the brine left a large interface. Additional tests were conducted to confirm the results on a homogenized emulsion. As shown below, demulsifier B produced a clear solvent phase under the more rigorous conditions. A final test to determine the effect of strong caustic (10% NaOH) on the demulsifiers also showed favorable results.

| Demul-sifier | Dose (ppm) | Aqueous Phase Clarity | Solvent Phase Clarity | Comments |
|---|---|---|---|---|
| B | 200 | Bad | Very good | Good* |
| B | 400 | Bad | Very good | Very good** |
| B | 600 | Bad | Very good | Very good** |
| B | 800 | Bad | Very good | Poor (10 ml)** |
| B | 1000 | Bad | Very good | Poor (12 ml)** |
| Nothing | | Bad | Very good | Very Poor (25 ml)* |
| Nothing | | Bad | Very good | Very Poor (25 ml)* |
| B | 400*** | 1 | 1 | Best Water Phase |
| B | 400**** | 2 | 1 | Best Water Phase |

*Acceptable solids at interface.
**Acceptable solids at interface; some solids at bottom.
***Not homogenized.
****Homogenized.

EXAMPLE 3

Tests on the following demulsifiers were conducted according to the procedure outlined in Example 1 above, but with a different pharmaceutical and emulsion. The emulsion was an emulsion of one part by weight filtered broth at pH 10.2 and 0.4 part by weight amyl alcohol. The demulsifiers were diluted with water to 10% by volume and added to a tube containing 50 ml of the emulsion. The tube was shaken 20 times to mix the contents and then centrifuged for four minutes.

| Demulsifier | Active Ingredient |
|---|---|
| G | quaternary condensed polyoxyalkylated amine derived from polyoxyethylated N-tallow-1,3-diaminopropane of m.w. about 650. Quaternization of nearly 100%; nearly complete water removal during condensation. |
| H | quaternary condensed polyoxyalkylated amine derived from polyoxyethylated long chain fatty diamine mixture of C-18, C-20 and C-22; m.w. about 500 to about 600. |

The following results were obtained:

| Demul-sifier | Dose (ppm) | Relative Volumes (ml) | | | Comments |
|---|---|---|---|---|---|
| | | Solvent | Interface | Aqueous | |
| Blank | — | Trace | 21 | 29 | |
| G | 2000 | Trace | 19 | 31 | |
| | 3000 | Trace | 18 | 32 | |
| | 4000 | 1 | 16 | 33 | |
| | 5000 | 13 | 3 | 35 | |
| | 6000 | 14 | 2 | 36 | |
| | 10000 | 14 | 1 | 38 | Solids flocculated before alcohol added |
| H | 2000 | Trace | 20 | 30 | |
| | 3000 | Trace | 18 | 32 | |
| | 4000 | 11 | 5 | 35 | Solvent slightly lighter than Demulsifier G |
| | 5000 | 14 | 2 | 36 | Solvent slightly lighter than Demulsifier G |
| | 6000 | 15 | 1 | 36 | Solvent slightly higher than Demulsifier G |
| | 10000 | 15 | 1 | 37 | Solvent slightly lighter than Demulsifier G |

NOTE:
Some volumes add to greater than 50 ml due to solvent added with demulsifier.

EXAMPLE 4

Tests on DEMULSO 1 demulsifier from Petrolite Corp. and the following demulsifiers were conducted according to the procedure outlined in Example 1 above. The emulsion contained a different pharmaceutical and was a "whole broth", i.e., not filtered, and so contained cell bodies. It had a pH of 3.0. The emulsion was one part by weight broth per 0.8 part by weight amyl acetate. The sample (50 ml) in each tube was homogenized for five minutes, diluted with amyl acetate to 10% by volume, shaken fifty times to mix and centrifuged for three minutes.

| Demulsifier | Active Ingredient |
|---|---|
| I | condensed polyoxyalkylated amine derived from polyoxyethylated N-tallow 1,3 diaminopropane of m.w. about 700. Nearly complete theoretical water removal during condensation. |
| J | condensed polyoxyalkylated amine derived from polyoxyethylated long chain fatty diamine mixture of C-18, C-20 and C-22 of m.w. about 500 to about 600. Nearly complete water removal during condensation. |
| K | polyoxyethylated amine of m.w. about 500 to about 600 derived from N-tallow-1,3-diaminopropane. |
| L | polyoxyethylated amine of m.w. about 600 derived from long chain fatty diamine mixture of C-18, C-20 and C-22. |

The following results were obtained:

| Demul- sifier | Dose (ppm) | Solvent | Interface | Aqueous | Solids |
|---|---|---|---|---|---|
| Blank | — | 0 | 42 | 18 | 0 |
| DEMULSO 1 | 500 | 13 | 25 | 12 | Trace |
|  | 1,000 | 18 | 19 | 13 | Trace |
|  | 3,000 | 19 | 21 | 10 | Trace |
|  | 10,000 | 18 | 22 | 10 | Trace |
| I | 500 | 3 | 38 | 9 | Trace |
|  | 1,000 | 18 | 20 | 12 | Trace |
|  | 3,000 | 20 | 20 | 10 | Trace |
|  | 10,000 | 20 | 20 | 10 | Trace |
| J | 500 | 1 | 40 | 9 | Trace |
|  | 1,000 | 10 | 30 | 10 | Trace |
|  | 3,000 | 17 | 20 | 13 | Trace |
|  | 10,000 | 18 | 19 | 13 | Trace |
| K | 500 | 13 | 27 | 10 | Trace |
|  | 1,000 | 19 | 19 | 12 | Trace |
|  | 3,000 | 19 | 20 | 11 | Trace |
|  | 10,000 | 18 | 20 | 12 | Trace |
| L | 500 | 1 | 41 | 8 | Trace |
|  | 1,000 | 16 | 24 | 10 | Trace |
|  | 3,000 | 19 | 20 | 11 | Trace |
|  | 10,000 | 19 | 21 | 10 | Trace |

EXAMPLE 5

Tests on Demulsifier G from example 3 above and the following demulsifiers were conducted according to the procedure outlined in Example 3 above.

| Demulsifier | Active Ingredient |
|---|---|
| M | quaternary polyoxyalkylated amine derived from polyoxyethylated N-tallow-1,3-diaminopropane of m.w. about 650. Quaternization of nearly 100%. |
| N | quaternary polyoxyalkylated amine derived from polyoxyethylated N-tallow-1,3-diaminopropane of m.w. about 700. Quaternization of nearly 100%. |
| O | quaternary polyoxyalkylated amine derived from polyoxyethylated N-tallow-1,3-diaminopropane of m.w. about 750. Quaternization of nearly 100%. |
| P | quaternary polyoxyalkylated amine derived from polyoxyethylated N-tallow-1,3-diaminopropane of m.w. about 900 to about 950. Quaternization of nearly 100%. |
| Q | quaternary condensed polyoxyalkylated amine derived from polyoxyethylated N-tallow-1,3-diaminopropane of m.w. about 700. Quaternization of nearly 100%; nearly complete water removal during condensation. |
| R | quaternary condensed polyoxyalkylated amine derived from polyoxyethylated N-tallow-1,3-diaminopropane of m.w. about 750. Quaternization of nearly 100%; nearly complete water removal during condensation. |
| S | quaternary condensed polyoxyalkylated amine derived from polyoxyethylated N-tallow-1,3-diaminopropane of m.w. about 900 to about 950. Quaternization of nearly 100%; nearly complete water removal during condensation. |

The following results were obtained:

| Demul- sifier | Dose (ppm) | Solvent | Interface | Aqueous | Solvent Clarity* | Aqueous Clarity* |
|---|---|---|---|---|---|---|
| Blank | — | 0 | 31 | 29 | — | VP |
| M | 4000 | 15 | 2 | 35 | ST | F |
| M | 6000 | 15 | 1.5 | 35.5 | ST | F |
| N | 4000 | 15 | 2 | 35 | ST | F |
| N | 6000 | 15 | 1.5 | 35.5 | ST | F |
| O | 4000 | 15 | 2 | 35 | ST | F |
| O | 6000 | 15 | 1.5 | 35.5 | ST | F |
| P | 4000 | 14 | 3 | 35 | ST | F |
| P | 6000 | 15 | 2 | 35 | ST | F |
| G | 4000 | 4 | 13 | 35 | G | P |
| G | 6000 | 12.5 | 4 | 35.5 | G | P |
| Q | 4000 | 10 | 7 | 35 | G | P |
| Q | 6000 | 13 | 3 | 36 | G | P |
| R | 4000 | 14 | 3 | 35 | VG | F |
| R | 6000 | 14 | 1.5 | 36.5 | ST | F |
| S | 4000 | 14 | 3 | 35 | G | F |
| S | 6000 | 15 | 2 | 35 | T | F |

*G = Good
P = Poor
T = Turbid
VG = Very Good
VP = Very Poor
ST = Slightly Turbid
F = Fair
NOTE:
Volumes may not add up to 50 due to demulsifier diluent addition.

In view of the above, it will be seen that several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for resolving emulsions produced in preparation of pharmaceuticals by fermentation and other such bioprocessing applications, comprising adding an effective amount of a demulsifier to an emulsion that includes both a pharmaceutical which is desired to be extracted from the emulsion and at least about 25% by weight of an organic solvent, said demulsifier comprising a nitrogen composition selected from the group consisting of (a) polyoxyalkylated amines that have been derived from amines having about six to about thirty carbon atoms, (b) polyoxyalkylated amines that have been quaternized to at least some extent and that have been derived from amines having about six to about thirty carbon atoms, (c) conjugate acid salts of polyoxyalkylated amines that have been derived from amines having about six to about thirty carbon atoms, (d) salts of polyoxyalkylated amines that have been quaternized to at least some extent and that have been derived from amines having about six to about thirty carbon atoms, (e) condensation product formed by heating an oxyalkylated amine under dehydration condensation conditions to produce a polyoxyalkylated amine of molecular weight of at least about 400, (f) conjugate acid salts of said condensation product, (g) said condensation product that has been quaternized to at least some extent, (h) conjugate acid salts of said condensation product that have been quaternized to at least some extent, (i) linear copolymers of an epihalohydrin and an amine selected from the group consisting of lower aliphatic primary amines having from about two to about eight carbon atoms and lower aliphatic secondary amines having from two to about eight carbon atoms, (j) such copolymers of an epihalohydrin and an amine wherein the amine is a lower aliphatic primary amine having from two to about eight carbon atoms, in which at least some of the nitrogen atoms of the copolymers therein have been quaternized, (k) polydialkyldiallyl ammonium salts, (l) polymers of acrylamido alkylene quaternary ammonium salts, and (m) mixtures thereof.

2. A method as set forth in claim 1 wherein said nitrogen composition is selected from the group consisting of (a) polyoxyalkylated amines that have been derived from amines having about six to about thirty carbon atoms, (b) polyoxyalkylated amines that have been quaternized to at least some extent and that have been derived from amines having about six to about thirty carbon atoms, (c) conjugate acid salts of polyoxyalkylated amines that have been derived from amines having about six to about thirty carbon atoms, and (d) salts of polyoxyalkylated amines that have been quaternized to at least some extent and that have been derived from amines having about six to about thirty carbon atoms.

3. A method as set forth in claim 1 wherein said nitrogen composition is selected from the group consisting of (i) polyoxyalkylated amines that have been quaternized to at least some extent and that have been derived from amines having about six to about thirty carbon atoms, (ii) conjugate acid salts of polyoxyalkylated amines that have been derived from amines having about six to about thirty carbon atoms, and (iii) salts of polyoxyalkylated amines that have been quaternized to at least some extent and that have been derived from amines having about six to about thirty carbon atoms.

4. A method as set forth in claim 1 wherein said nitrogen composition is selected from the group consisting of said condensation product and conjugate acid salts of said condensation product.

5. A method as set forth in claim 4 wherein the amine is selected from the group consisting of monoamines, diamines and triamines having at least one substitution of from about six to about 22 carbon atoms, and the condensed polyoxyalkylated amine has a molecular weight of at least about 1000.

6. A method as set forth in claim 5 wherein said amine is $C_{18}H_{35}NH_2$.

7. A method as set forth in claim 1 wherein said nitrogen composition is a quaternary of said condensation product, said quaternary having been formed by reacting said condensation product with an alkylating agent.

8. A method as set forth in claim 7 wherein said alkylating agent is selected from the group consisting of methyl chloride and benzyl chloride.

9. A method as set forth in claim 7 wherein the quaternary comprises a nitrogen and four organic radicals extending therefrom and each organic radical has from about twelve to about 22 carbon atoms.

10. A method as set forth in claim 1 wherein said nitrogen composition is a conjugate acid salt of said quaternary of said condensation product.

11. A method as set forth in claim 1 wherein said nitrogen composition is a copolymer of an epihalohydrin and an amine selected from the group consisting of lower aliphatic primary amines having from two to about eight carbon atoms and lower aliphatic secondary amines having from two to about eight carbon atoms.

12. A method as set forth in claim 11 wherein said amine is a monoamine and said epihalohydrin is epichlorohydrin, and the mole ratio of epichlorohydrin to monoamine in the copolymer is in the range of from about 0.75 to about 1.0.

13. A method as set forth in claim 12 wherein said copolymer is a copolymer of dimethylamine and epichlorohydrin and has a molecular weight of from about 200 to about 50,000.

14. A method as set forth in claim 1 wherein said nitrogen composition is a copolymer of an epihalohydrin and a lower aliphatic primary monoamine having one amino group and from two to about eight carbon atoms.

15. A method as set forth in claim 14 wherein the nitrogen atoms of the nitrogen composition have been quaternized with a lower alkyl halide.

16. A method as set forth in claim 1 wherein said nitrogen composition is a poly-dialkyldiallyl ammonium chloride.

17. A method as set forth in claim 16 wherein said poly-dialkyldiallyl ammonium chloride is poly-dimethyldiallyl ammonium chloride having a molecular weight of at least about 10,000.

18. A method as set forth in claim 1 wherein said nitrogen composition is a polymer of an acrylamido alkylene quaternary ammonium salt.

19. A method as set forth in claim 18 wherein said nitrogen composition is a polymer of methacrylamido alkylene quaternary ammonium salt.

20. A method as set forth in claim 18 wherein said nitrogen composition has a molecular weight of from about 100,000 to about 2,000,000.

* * * * *